United States Patent
Dauser

(10) Patent No.: US 8,992,735 B2
(45) Date of Patent: Mar. 31, 2015

(54) METHOD AND DEVICE FOR THE HYDROLYSIS OF PREFERABLY SOLID ORGANIC SUBSTRATES

(75) Inventor: Hermann Dauser, Wals Siezenheim (AT)

(73) Assignee: Biogas Systems GmbH, Parndorf (AU)

( * ) Notice: Subject to any disclaimer, the term of this patent is extended or adjusted under 35 U.S.C. 154(b) by 0 days.

(21) Appl. No.: 13/699,651

(22) PCT Filed: Mar. 15, 2011

(86) PCT No.: PCT/EP2011/053864
§ 371 (c)(1),
(2), (4) Date: Dec. 20, 2012

(87) PCT Pub. No.: WO2011/147601
PCT Pub. Date: Dec. 1, 2011

(65) Prior Publication Data
US 2013/0206345 A1    Aug. 15, 2013

(30) Foreign Application Priority Data

May 25, 2010   (AT) .................................. A 853/2010

(51) Int. Cl.
*D21C 7/06* (2006.01)
*D21C 1/02* (2006.01)
(Continued)

(52) U.S. Cl.
CPC ................ *D21C 1/02* (2013.01); *C12M 21/04* (2013.01); *C12M 33/16* (2013.01); *C12M 45/04* (2013.01); *C12M 45/20* (2013.01); *D21B 1/36* (2013.01); *C12M 45/02* (2013.01); *C12M 29/24* (2013.01)
USPC ......................................... 162/246; 162/250

(58) Field of Classification Search
CPC ........... D21C 1/02; D21C 7/06; C12M 33/16; C12M 34/06; C12M 45/20
USPC .................................................... 162/246, 250
See application file for complete search history.

(56) References Cited

U.S. PATENT DOCUMENTS 2,086,701 A * 7/1937 Dreyfus .......................... 127/37
2011/0100359 A1* 5/2011 North ............................... 127/1

FOREIGN PATENT DOCUMENTS

AT         507469 B1 *  8/2010
GB        1011891 A  *  1/1962

OTHER PUBLICATIONS

Smook, Handbook for Pulp and Paper Technologists, 1992, Angus Wilde Publications, 2nd edition, Chapters 3 and 8.*

(Continued)

*Primary Examiner* — Anthony Calandra
(74) *Attorney, Agent, or Firm* — Jordan IP Law, LLC; Todd A. Vaughn

(57) ABSTRACT

The invention relates to a device for the hydrolysis of preferably solid organic substrates, in particular of energy crops and plant residues, with a collection vessel (1) for receiving the organic substrates, with a conveying means (4) for transporting the organic substrates into a charging device (7) for the batch-wise charging of a hydrolyzer (10) with the organic substrates, the hydrolyzer (10) being provided on the output with a pressure-release device (12) having a valve-controlled pressure diaphragm (13) and a steam trap (14) arranged upstream of an expander tank (15). According to the invention, the conveying means (4) includes a conveyor worm (4') with a sleeve shaft (25), which is charged with hot steam from the steam trap (14), which is preferably designed as a cyclone, the sleeve shaft (25), in the conveying zone for the organic substrate, having, in a heating zone (18), steam-outlet openings (26) for directly charging the organic substrate with hot steam.

12 Claims, 4 Drawing Sheets

(51) Int. Cl.
*C12M 1/107* (2006.01)
*C12M 1/26* (2006.01)
*C12M 1/00* (2006.01)
*D21B 1/36* (2006.01)
*C12M 1/33* (2006.01)

(56) References Cited

OTHER PUBLICATIONS

Google Machine Translation of AT507469B1, Aug. 2010, translation performed Jun. 12, 2014.*

* cited by examiner

METHOD AND DEVICE FOR THE HYDROLYSIS OF PREFERABLY SOLID ORGANIC SUBSTRATES

CROSS-REFERENCE TO RELATED APPLICATIONS

The present application is a National Stage Application of PCT International Application No. PCT/EP2011/053864 (filed on Mar. 15, 2011), under 35 U.S.C. §371, which claims priority to Austrian Patent Application No. A 853/2010 (filed on May 25, 2010), which are each hereby incorporated by reference in their respective entireties.

FIELD OF THE INVENTION

The invention relates to a method and apparatus for hydrolysis of preferably solid organic substrates, in particular energy crops and vegetable waste, which comprises a collecting bin for receiving organic substrates, and conveying means for transporting the organic substrates to a charging device for batchwise filling of a hydrolizer with the organic substrates, said hydrolizer being provided on the output side with a depressurizing unit with a valve-controlled pressure baffle and a steam separator upstream of a flash tank.

BACKGROUND OF THE INVENTION

Methods and apparatus of this kind are used for pretreatment of organic substrates, which after having passed a hydrolizer (a device for thermal pressure hydrolysis) are fed into a fermenter, for instance a biogas or biofuel plant.

Thermal pressure hydrolysis uses a technology called "steam explosion," which is known from biogas and biofuel plants. "Steam explosion" is a technical process in which the input material is heated up to 300° C., preferably 150° C. to 200° C., and exposed to a pressure of 3 bar up to 20 bar. This pressure-temperature state is upheld for a certain period of time, after which the substrate is suddenly depressurized to atmospheric pressure. Due to this depressurization shock the cell substance is completely broken down. All of the organic substance is then present in liquified form for further processing.

The initially inhomogeneous substrate mixture (for instance, energy crops, harvesting waste etc.) is transformed into a homogeneous pulp having the following properties: cellulose is set free; crusts of hemicellulose-lignin complexes are broken down; hemicellulose is cooked; yeast, mildew and other undesirable microorganisms are destroyed; the substrate is sterilized; and fibrous matter is destabilized.

Prior to further substrate processing, for instance in a biogas plant, "steam explosion" thus takes care of the process steps of hydrolysis and homogenization. Fermentation conditions may thus be specifically optimized for processes of acido/acetogenesis and methanogenesis.

The result of such pretreatment is an increased substrate yield and improved product quality, in the case of a biogas plant a higher substrate decomposition rate with increased gas production and improved gas quality. Typically, specific methane content ($CH_4$) is increased while noxious hydrogen sulfide content ($H_2S$) is reduced.

U.S. Patent No. 2003/0121851 A1 describes a method and apparatus for treating biologically degradable organic waste. Before the organic waste is submitted to thermal pressure hydrolysis an alkaline solution (KOH) is added to the substrate and the substrate is subjected to temperatures of 170° C. to 225° C. and correlated vapour pressure in the hydrolizer. Solid/liquid separation is then carried out. Prior to treatment the substrate may be preheated in a tank by recycled steam from the hydrolizer.

From WO 2008/011839 A2 there has for instance become known a plant for continuous and discontinuous hydrolysis of organic substrates. The plant essentially comprises a shredder for the inhomogeneous organic substrate, from which the substrate is fed to a metering charger for the hydrolizer. After treatment of the substrate in the hydrolizer it is conveyed via an "overshooting pipe" into a flash tank, from which an exhaust gas line leads to a condenser and a substrate line leads to a fermenter. The exhaust gases are fed into a steam condenser, which is water-cooled, and the condensate obtained by this step is recycled to the flash tank. The substrate line to the fermenter contains a heat exchanger whose waste heat is supplied via an external heat exchanger circuit to a heat exchanger used as preheating device, which will heat the input substrate coming from the shredder.

From SU 1620487 A1 there is known a hydrolizer having two concentric screw conveyors in a cylindrical housing, between which a drum screen is disposed. The organic material enters an outer cylindrical annular chamber via a feeder pipe and is compressed by the first screw conveyor, with superheated steam being fed into the outer annular chamber via a steam line. Then the material arrives in the inner hollow space where it is transported in reverse direction to an exit opening by the second screw conveyor.

The known methods and apparatus suffer from the disadvantage of not being energetically optimized and having a relatively complex structure.

In this context there has become known from EP 2 177 280 an apparatus for discontinuous hydrolysis of organic substances, which comprises the following components: a liquid-filled preconditioning tank for receiving solid floatable organic substrates, with an agitator and a steam distributor unit, configured as a special jet stock for creating a flotation effect; a screw conveyor for taking organic substrate from a floating mat building up on the surface, with an integrated sieve unit and a recirculation line for recirculating the filtrate; a charger unit with a pressure vessel (blow gun) and a charger gate and an additional valve-controlled connecting line to the hydrolizer; a transfer pump for taking liquid from the preconditioning tank and feeding it to the charger unit; a hydrolizer with agitator for carrying out thermal pressure hydrolysis; a valve-controlled depressurizing unit with a pressure baffle, a cyclone; and a flash tank with integrated heat exchanger.

The apparatus known from EP 2 177 280 is suitable in particular for the processing of substrates and substrate mixtures with a certain liquid content or admixture of liquid, where the floatable solid components are separated by rinsing or flotation prior to charging the hydrolizer. It is a disadvantage that reliable balancing of substrate intake is not possible due to the uncontrolled intake of liquid of the solid component during the pulping process.

SUMMARY OF THE INVENTION

It is an object of the present invention to optimize an apparatus for hydrolysis of relatively dry organic substrates with regard to both operation and energy management, while still achieving a compact design.

In accordance with the invention this object is achieved by proposing that the conveyor means comprise a screw conveyor with a hollow shaft, into which is fed superheated steam from the steam separator, which is preferably configured as a cyclone, the hollow shaft having steam vents in a heating zone in the conveying area for the organic substrate for directly subjecting the organic substrate to superheated steam. Through these steam vents in the hollow shaft the organic substrate is effectively and uniformly exposed to steam already prior to entry into the hydrolizer, and by using waste steam from the steam separator energy is conserved.

The apparatus may be further energetically optimized by providing the heating zone of the conveyor screw with a connecting line to the collecting bin for the organic substrate, through which the superheated steam exiting from the heating zone is fed into the collecting bin and will pass on into a storage bunker if provided.

Operationally, the apparatus is optimized by metered addition of process water, the charger unit of the hydrolizer being furnished according to the invention with a metering unit for process water to enable sufficient watering of the organic substrate prior to entry into the hydrolizer. For heating the process water a heat exchanger is provided, which is in thermal contact with the flash tank, thus permitting recovery of the waste heat of the flash tank.

In the method of the invention superheated steam is separated from the substrates treated by thermal pressure hydrolysis immediately upon discharge of a partial batch and flashing, and is used for heating the organic substrate input in the hydrolysis process, the separated superheated steam being directly blown into a conveyor screw, which feeds the organic substrate to the thermal pressure hydrolysis process.

In accordance with the invention the initially dry substrate absorbs the condensation heat of the superheated steam in the screw conveyor and is heated to 70° C., preferably to 100° C., and is additionally steamed, whereby the surface structures of the substrate are softened and water is absorbed. By the simultaneous motion of the conveyor screw during the steaming process the contact between the media is intensified.

BRIEF DESCRIPTION OF THE DRAWINGS

The invention will now be described in more detail referring to the enclosed schematic drawings. There is shown in.

DETAILED DESCRIPTION OF EMBODIMENTS

Figure 1:
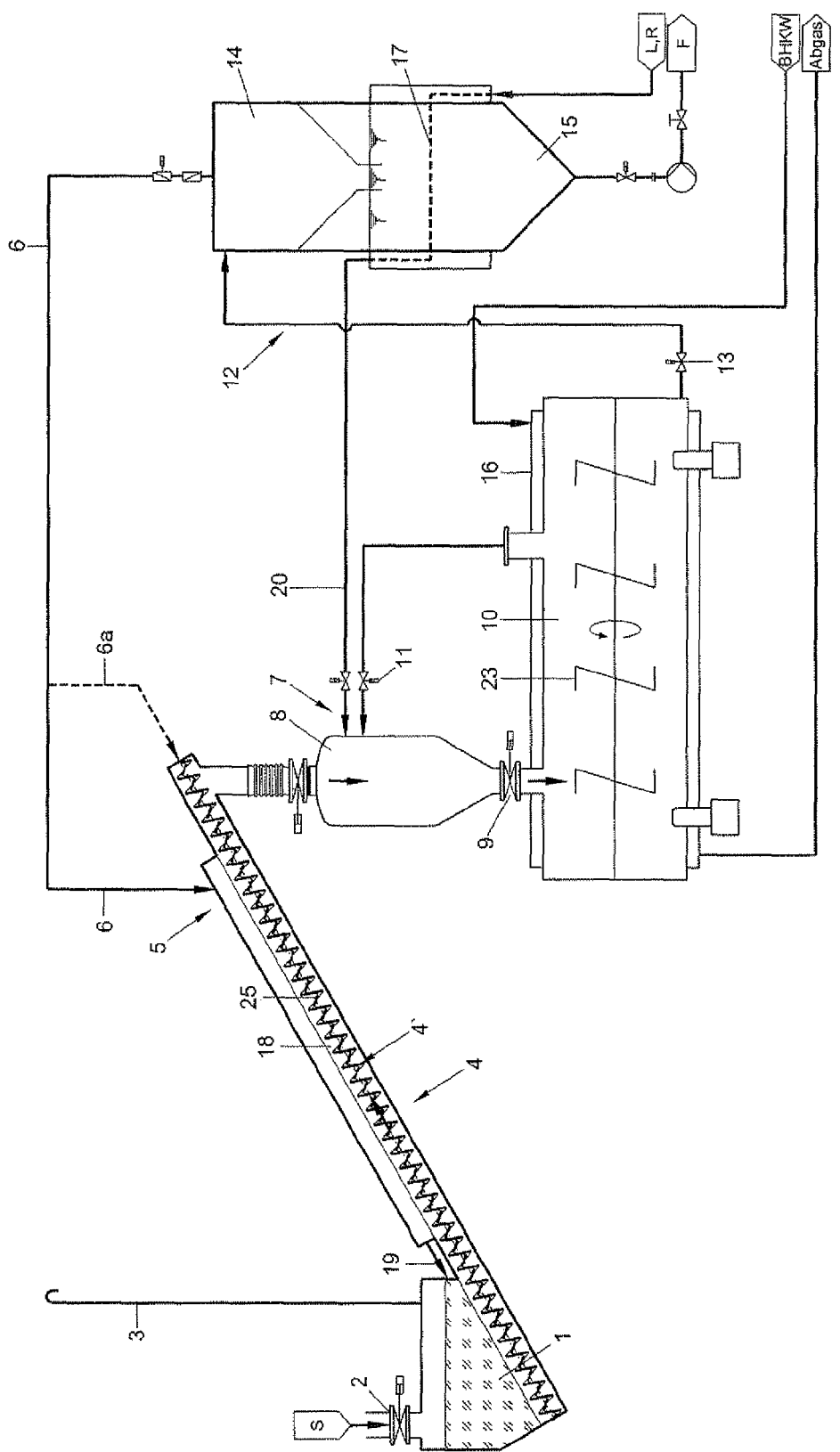
FIG. 1 illustrates an apparatus for hydrolysis of preferably solid, organic substrates in accordance with the invention.

The apparatus for hydrolysis of organic substrates shown in FIG. 1 essentially comprises the following components: a collecting bin 1 for receiving solid organic substrates, for instance shredded straw or silage, with an intake opening 2 for the substrate and a waste steam line 3; a conveyor means, such as a screw conveyor 4 for transporting organic substrates, with a heating unit 5, which receives superheated steam from the steam separator 14 via a line 6; a charging device 7 with a pressure vessel 8 (blow gun) plus valve-controlled charging port 9 into the hydrolizer 10 and a valve-controlled connecting line 11 to the hydrolizer 10; a hydrolizer 10 for carrying out thermal pressure hydrolysis including an agitator 23; a depressurization unit 12 with a valve-controlled pressure baffle 13, a steam separator 14 (i.e. a cyclone) leading to a flash tank 15; a unit 16 for heating of the hydrolizer 10; and a flash tank 15 with integrated heat exchanger 17.

The screw conveyor 4 passes through a closed heating zone 18 of the heating unit 5, into which superheated steam from the steam separator 14 configured as a cyclone, is fed via the steam line 6.

Furthermore, the heating zone 18 of the screw conveyor 4 may be provided with a connecting line 19 to the collecting bin 1 for the organic substrate, through which superheated steam exiting from the heating zone 18 flows into the collecting bin 1 and preheats the substrate stored there.

Figure 3:
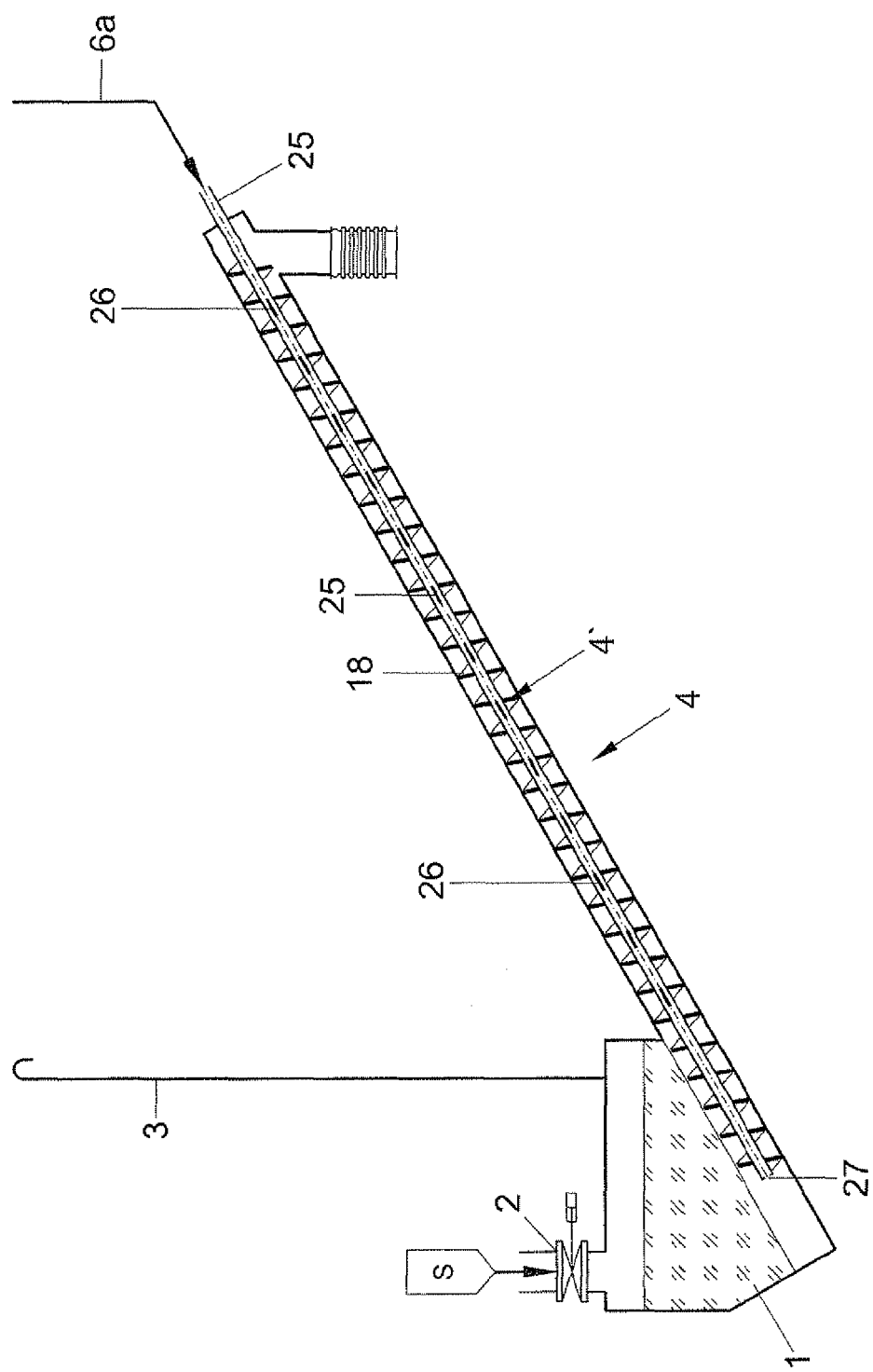
FIG. 3 illustrates a detail of the apparatus of FIGS. 1 and 2.

In accordance with a detail of the invention shown in FIG. 3, the screw conveyor 4 is provided with a hollow shaft 25, into which is fed via line 6a superheated steam from the steam separator 14 preferably configured as a cyclone. The superheated steam may also be fed directly into the hollow shaft 25 by means of the steam line 6 (see FIG. 4). In the conveyor area for the organic substrate the hollow shaft 25 has slit-shaped steam vents 26, which will permit effective, uniform steaming of the substrate.

At the end of the hollow shaft 25 of the screw conveyor 4, which dips into the collecting bin 1, there is provided a preferably valve-controlled exit opening 27 for venting surplus superheated steam into the collecting bin 1.

Description of the Process

The substrate present in the collecting bin 1 usually consists of material in the form of short fibers or crumbs with a particle size of up to 5 cm, typically with 30% (e.g. silage) to 90% (e.g. straw) of dry substance.

The screw conveyor 4 takes substrate from the collecting bin 1 and transports it to the charging unit 7 of the hydrolizer 10. (The amount of substrate present in the screw conveyor 4 at a typical filling level practically corresponds to a batch charge of the hydrolizer 10 and at the same time to a filling of the collecting bin 1).

Collecting bin 1 and screw conveyor 4 are designed such that superheated steam from the flashing process of the depressurization unit 12 may be directly fed to the substrate contained in there via a distribution and feeder device of the heating unit 5, in particular the steam vents in the hollow shaft 25. Condensation heat transferred when the steam contacts the substrate will heat the substrate up to 100° C., typically to more than 70° C. This will significantly reduce the heating effort required to reach the operating point of the hydrolizer 10, i.e. up to 180° C.

An additional positive effect lies in the steaming of the substrate, that is in the softening of the surface structures and the absorption of water by the substrate. Humid air or residual steam passes from the heating zone 18 to the collecting bin 1 or is expelled as waste air.

The screw conveyor 4 sequentially transports a defined amount of preheated and humidified substrate into the pressure vessel 8 of the charging unit 7. When the required filling level of substrate is reached a defined volume of process water is additionally metered into the pressure vessel 8 via a metering unit 20 to achieve a sufficiently watered substrate mixture. In order to reduce the heating effort required for the hydrolizer 10 this process water is preheated to between 50° C. and 100° C. by the heat exchanger 17 in the flash tank 15.

This kind of sequential charging permits accurate control of the mass flows entering the hydrolizer 10, separately for the substrate and the process water. This will enable targeted setting of operational parameters and system throughput.

The pressure vessel 8 of the charging unit 7 is a so-called "blow gun", i.e. after filling with a charge the vessel is tightly closed against the ambient atmosphere by shutting the intake opening, and is brought to the system pressure of the hydrolizer 10 by opening a valve-controlled connecting line 11. The valve of the connecting line 11 is then again closed.

The pressure vessel 8 is emptied cyclically via the valve-controlled charging port 9 by the pressure difference between pressure vessel 8 and hydrolizer 10 (usually 1 to 2 bar) arising when the hydrolizer has been partly emptied. If required, system pressure may be increased by introducing compressed air into the pressure vessel 8 to ensure complete emptying of the charging unit 7.

After filling of the hydrolizer 10 by means of the "blow gun" the hydrolysing process will proceed under continuous heating via a heating unit 16 and simultaneous pressure increase, for a certain retention period of e.g. 30 minutes up to some hours.

A defined volume will then be discharged by excess system pressure and will be disintegrated in the depressurization unit 12 by spontaneous flashing and a pressure shock.

Charging and discharging of the substrate into and from the hydrolizer 10 is carried out in a sequence of short cycles, for instance 2 to 4 cycles per hour, each addressing only part of the hydrolizer volume, for instance 10% to 30%. This particular mode of operation with a rapid series of charging and discharging cycles for part of the reactor volume will subsequently be called quasi-continuous.

Quasi-continuous operation has a number of decisive advantages over known continuous or discontinuous processes. a) Due to batchwise discharge the pressure baffle 13 can have large diameter with high throughput, thus avoiding wear and damage to the baffle and congestions, which typically occur in continuous processes; b) By discharging each time only part of the hydrolizer volume all of the substrate is discharged with maximum flash effect or "degree of severity," resulting in optimum disintegration of the substrate. Classical discontinuous batch processes with total reactor discharge in each cycle suffer from an unavoidable residuum of less disintegrated substrate, since the excess pressure driving the discharge will decrease continuously as the reactor discharge progresses. c) Classical batch processes due to their operational mode require cyclical heating, which means high power peaks and a discontinuous consumption of heating medium. In quasi-continuous operation of the hydrolizer 10 heating power will permanently be constant, which will conform to the typical operation of a biogas plant.

Heating of the hydrolizer 10 usually is effected by steam, thermal oil or a gas burner. In case the system is combined with a biogas plant with co-generation (generation of electric power and waste heat in a combined heat and power plant CHP or a similar internal combustion system)—a typical plant configuration—a device for feeding hot waste gas from co-generation may be used for directly heating the hydrolizer 10. This will achieve further energy optimization of the system.

The substrate exiting the hydrolizer 10, which is largely disintegrated or liquified, enters a cylone 14, where a gas component (superheated steam) is separated while the liquid/solid component flows downwards into the flash tank 15.

By a shell-and-tube or plate-type heat exchanger 17 in the flash tank 15, the high system temperature of the substrate (approx. 100° C.) may be exploited, for instance to preheat the process water used for liquid enrichment in the pressure vessel 8.

From the flash tank 15 the treated substrate is removed for further processing by a suitable conveying means (for instance a thick matter pump).

Figure 2:
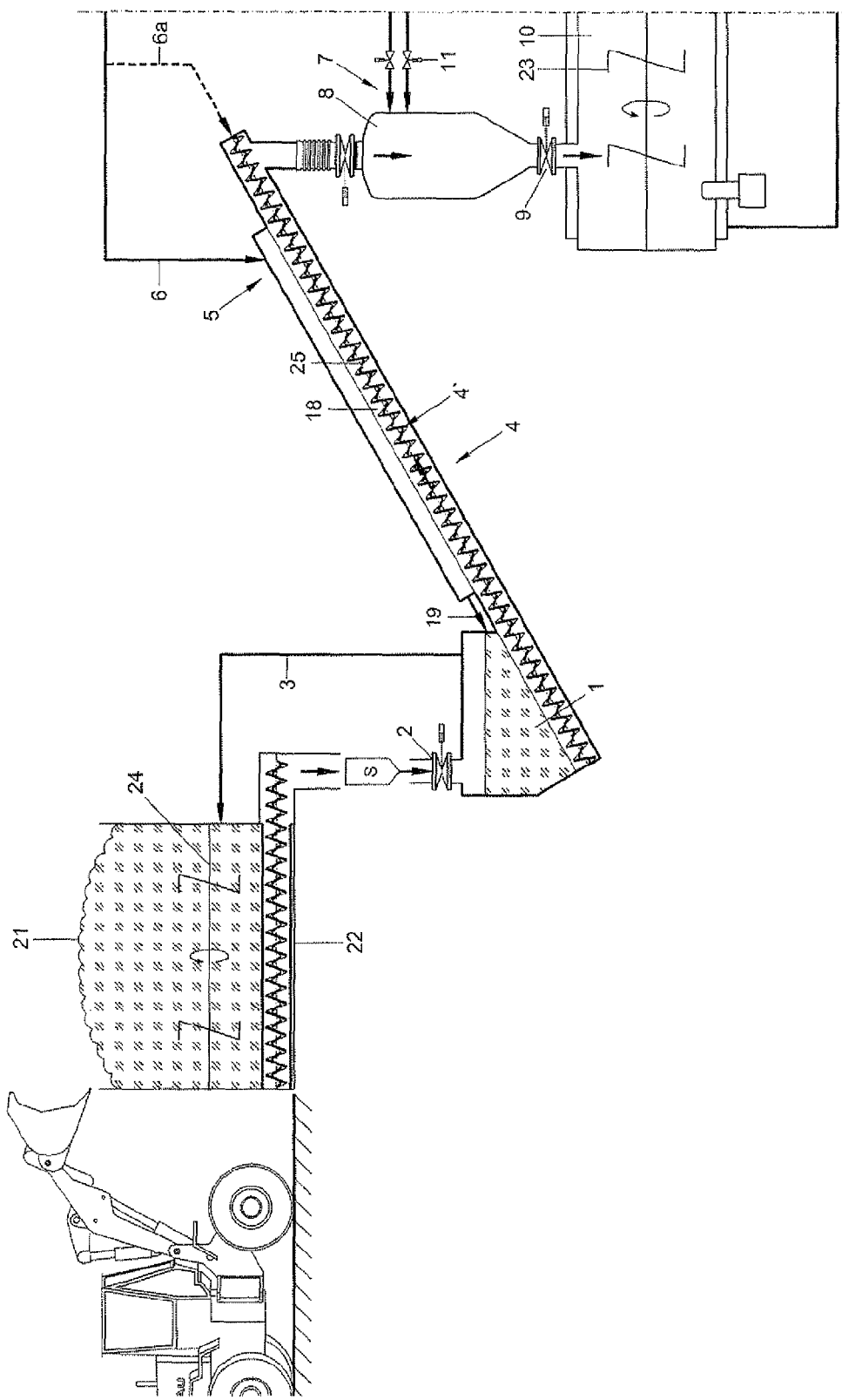
FIG. 2 illustrates a variant in accordance with the invention of the apparatus of FIG. 1.

In the variant of the invention shown in FIG. 2 the collecting bin 1 receiving the organic substrate is preceded by a storage bunker 21 with a mixer 24 and a conveyor 22. The mixer 24 destroys substrate agglomerations, which would inhibit further entry of the substrate into the conveyor 22. The rotational motion of the mixer 24 can also optimize the feeding of the substrate into the conveyor.

By directing the waste steam line 3 from the collecting bin 1 into the storage bunker 21 residual steam may once more be used to preheat the substrate. The pressure shock of the entering steam will additionally loosen the substrate in the bunker, which helps to avoid agglomerations in the substrate.

Figure 4:
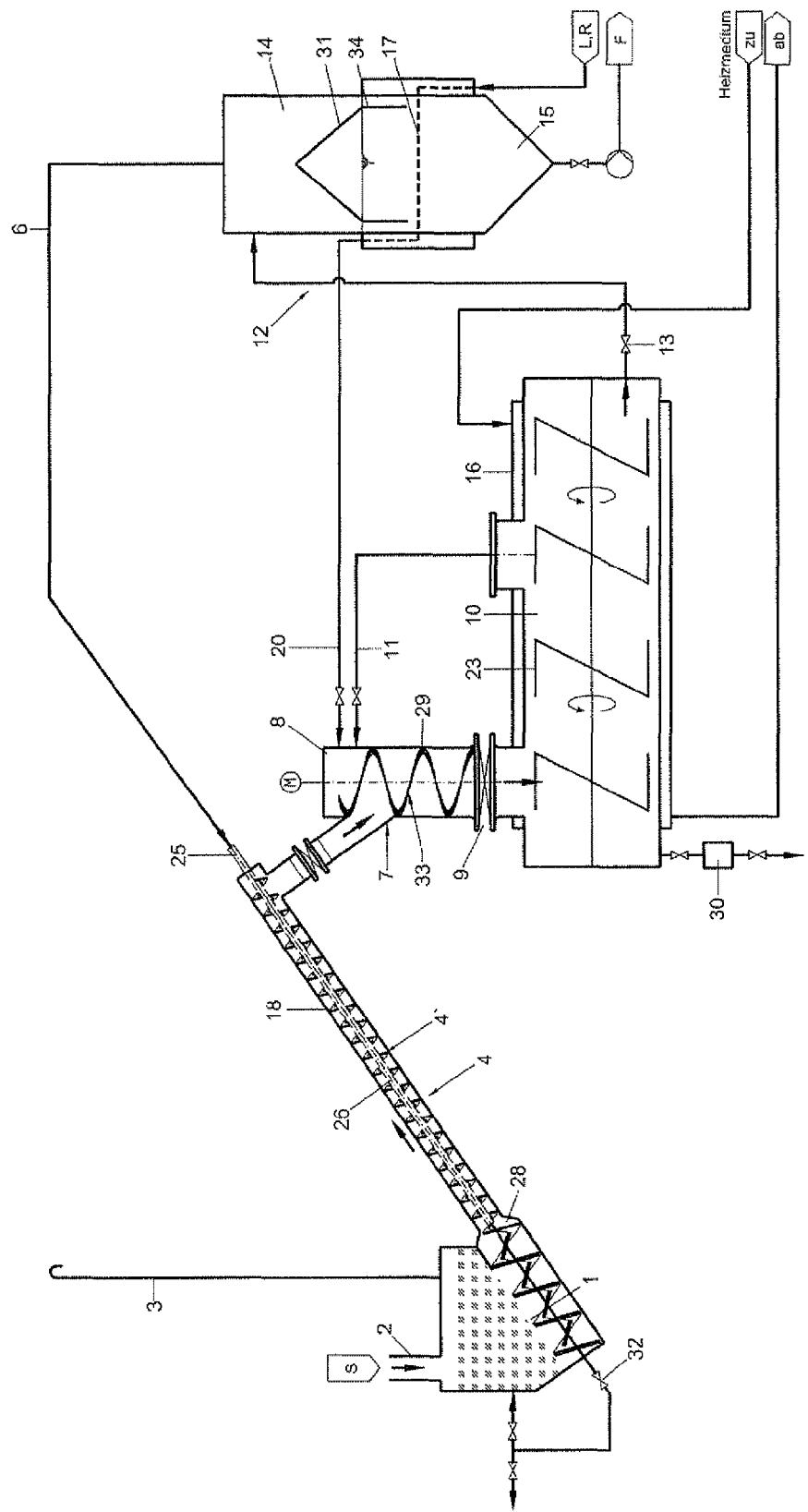
FIG. 4 illustrates a further variant in accordance with the invention of the apparatus of FIG. 1.

In the variant in accordance with FIG. 4 the hollow shaft 25 with steam vents 26 of the screw conveyor 4' has at its bottom end a switching valve 32, through which solid or liquid substrate that has entered the hollow shaft 25 through the steam vents 26, will be removed. This is done cyclically by the input of recycled waste steam from the steam separator 14 via the connecting line 6. By its excess pressure material deposited inside the hollow shaft 25 is blown out through the opened switch valve 32 and returned either to the collecting bin 1, the storage bunker 21 (not shown here, see FIG. 2), or some other collector unit. Congestion of the hollow shaft 25 or its steam vents 26 by substrate particles will thus be avoided.

Furthermore the switch valve 32 permits flushing with cleansing media or compressed air. The switch valve 32 may additionally be used to feed a surplus of process steam into the collecting bin 1 or the storage bunker 21 and to relieve excess pressure in the heating zone 18.

Loose substrate such as shredded straw and silage may have very low bulk density, such that the substrate mass in the screw conveyor 4 respectively in the heating zone 18 will not be sufficient for a complete batch filling of the charging unit 7 and the desired total filling of the tubular heating zone 18 cannot be achieved.

To avoid this situation the screw conveyor 4' has a larger diameter in the area of the collecting bin 1 than in the heating zone 18, resulting in a compactification zone 28 at the transition to the heating zone 18, in which the transported material is compacted. The screw flight of the conveyor is for instance varied in such a way that the diameter of the screw is reduced at a ratio of 2:1 at the transition to the heating zone 18, leading to compact filling of the screw flight in the heating zone 18. This compactification does not create excess pressure, it simply increases substrate density.

Practical experiments have shown that in the instance of "bulky" fibrous substrates being put into the pressure vessel 8 (blow gun) of the charging unit 7, in particular at low rates of exchange, pressure equalization between hydrolizer 10 and blow gun 8 prior to discharge will not be sufficient to reliably ensure fast and complete emptying of the blow gun.

This problem may be solved by disposing in the pressure vessel 8 of the charging unit 7 a rotatable clearing screw 29, in the form of a narrow helical metal strip 33 along the inner wall of pressure vessel 8, that will not impede the filling process. The clearing screw 29 is rotated during the charging process of the hydrolizer 10 with transport direction downwards and causes substrate adhering to the wall of the pressure vessel 8 to be scraped off, resulting in a brisk downward movement even at low system excess pressure, which will guarantee fast and complete emptying of the blow gun. The clearing screw 29 itself does not create excess pressure since it is not a compacting screw, and the installation is not prone to wear or failure.

Since the substrates to be treated mostly come from agricultural sources it cannot be excluded that heavy foreign objects such as stones or small metal parts will enter the system. Since the overall system preferably works without prior screening or removal, such substances will accumulate over time in the hydrolizer 10, as they cannot escape due to quasi-continuous partial charging and discharging and as the connection to the depressurization device 12 is not usually located in the immediate vicinity of the hydrolizer bottom.

In order to avoid the building-up of sediment which might cause damage, an effective removal system for such foreign substances is provided. Preferably, the hydrolizer 10 is connected via a valve to a sediment chamber 30, which is opened during the removal process and is then closed again. After pressure equalization against the ambient atmosphere the sediment chamber 30 may be emptied via a second valve. In this way removal of deposited foreign objects can be carried out while the system is in operation.

The high temperature of the substrate discharged from the hydrolizer 10 and transferred to the cyclone or steam separator 14 is exploited for preheating process water or other liquids. Heat transfer in the area of the heat exchanger 17 may be optimized by actively guiding the hot substrate flowing from the cylone 14 into the flash tank 15 to the heat transfer surface, in this case preferably the wall of the tank.

This will preferably be done by providing the steam separator with an internal cone 31 joined to a cylindrical area 34, which forms an annular gap with the tank wall, the depressurization device 12 opening tangentially into the steam separator 14. The typical design of a cyclone with the tip of the cone pointing downwards to a central outlet (see FIG. 1) is here inverted, letting the substrate flow downwards in the annular gap at the outer periphery of the cone 31. This fits in well with the tangential charging of the cyclone leading to peripheral distribution of the liquid substrate along the cyclone wall. The hot substrate flows directly along the heating surface of the heat exchanger 17 prior to mixing with the other material in the flash tank 15.

What is claimed is:

1. An apparatus for hydrolysis of solid, organic substrates, the apparatus comprising:
   a collecting bin configured to receive the solid, organic substrates;
   a hydrolizer configured to carry out thermal pressure hydrolysis;
   a charging device configured to batchwise fill the hydrolizer with the solid, organic substrates;
   a depressurization unit provided on an output side of the hydrolizer and having a valve-controlled pressure baffle and a steam separator upstream of a flash tank; and
   a conveyor configured to transport the solid, organic substrates to the charging device,
   wherein the conveyor is provided with a screw conveyor having a hollow shaft, into which is fed superheated steam from a steam separator, the hollow shaft having steam vents in a heating zone in a conveying area for the solid, organic substrate, and by which the solid, organic substrate is directly subjected to superheated steam,
   wherein an end of the hollow shaft is provided with a valve-controlled exit opening configured to feed the superheated steam directly into the collecting bin.

2. The apparatus of claim 1, wherein the conveyor screw has a larger diameter in the area of the collecting bin than in the heating zone, resulting in a compactification zone at a transition to the heating zone, in which transported solid, organic substrate is compacted.

3. The apparatus of claim 1, further comprising a metering unit for process water operatively connected to the charging unit, the metering unit configured to provide the process water to the solid, organic substrate prior to entry of the solid, organic substrate into the hydrolizer.

4. The apparatus of claim 3, further comprising:
   a tank operatively fluidically connected to the metering unit and configured to receive the process water;
   a heat exchanger configured to heat the process water and which is in thermal contact with the tank.

5. The apparatus of claim 1, wherein the steam separator has an internal cone with an adjoining cylindrical area which forms an annular gap with a container wall such that the depressurization unit enters the steam separator tangentially.

6. The apparatus of claim 1, wherein the charging unit has a pressure vessel, which, besides a valve-controlled charging port into the hydrolizer, has a valve-controlled connecting line for temperature and pressure equalization with the hydrolizer.

7. The apparatus of claim 6, further comprising a rotatable clearing screw disposed in the pressure vessel of the charging unit, and which comprises a helical metal strip along the inner wall of pressure vessel.

8. The apparatus of claim 1, further comprising a sediment chamber connected via a valve to the hydrolizer and which is configured to receive foreign objects removed from the hydrolizer.

9. The apparatus of claim 1, further comprising:
   a storage bunker provided upstream of the collecting bin and configured to receive the solid, organic substrates;
   a second conveyor operatively connected to the storage bunker;
   a waste steam line operatively connected between the collecting bin and the storage bunker.

10. An apparatus for hydrolysis of organic material, the apparatus comprising:
    a first bin configured to receive the organic material;
    a first conveyor operatively connected to the first bin;
    a second bin configured to receive the organic material from the first bin via the first conveyor;
    a second conveyor operatively connected to the second bin;
    a charging device configured to receive the organic material from the second bin via the second conveyor;
    a hydrolizer configured to receive the organic material from the charging device and carry out thermal pressure hydrolysis on the organic material; and
    a waste steam line operatively connected between the first bin and the second bin,
    wherein the conveyor is provided with a hollow shaft configured to receive superheated steam, the hollow shaft having steam vents by which the organic material is directly subjected to superheated steam.

11. The apparatus of claim 10, further comprising a valve-controlled exit opening at an end of the hollow shaft, the valve-controlled exit opening configured to feed the superheated steam directly into the second bin.

12. An apparatus for hydrolysis of solid, organic substrates, the apparatus comprising:
    a collecting bin configured to receive the solid, organic substrates;
    a hydrolizer configured to carry out thermal pressure hydrolysis;
    a charging device configured to batchwise fill the hydrolizer with the solid, organic substrates;
    a depressurization unit provided on an output side of the hydrolizer and having a valve-controlled pressure baffle and a steam separator upstream of a flash tank;
    a conveyor configured to transport the solid, organic substrates to the charging device, the conveyor being provided with a screw conveyor having a hollow shaft, into which is fed superheated steam from a steam separator, the hollow shaft having steam vents in a heating zone in a conveying area for the solid, organic substrate, and by which the solid, organic substrate is directly subjected to superheated steam; and
    a switch valve at an end of the hollow shaft and through which the solid, organic substrate can be removed that has entered the hollow shaft through the steam vents.

* * * * *